United States Patent
Kokubun

(10) Patent No.: US 8,755,565 B2
(45) Date of Patent: Jun. 17, 2014

(54) X-RAY CT APPARATUS AND IMAGE DISPLAY METHOD OF X-RAY CT APPARATUS

(75) Inventor: Hiroto Kokubun, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 252 days.

(21) Appl. No.: 13/504,164

(22) PCT Filed: Nov. 4, 2010

(86) PCT No.: PCT/JP2010/069570
§ 371 (c)(1),
(2), (4) Date: Apr. 26, 2012

(87) PCT Pub. No.: WO2011/055742
PCT Pub. Date: May 12, 2011

(65) Prior Publication Data
US 2012/0207355 A1    Aug. 16, 2012

(30) Foreign Application Priority Data

Nov. 4, 2009  (JP) ................................ 2009-252808

(51) Int. Cl.
*G06K 9/00*  (2006.01)
(52) U.S. Cl.
USPC .......................................................... 382/103
(58) Field of Classification Search
None
See application file for complete search history.

(56) References Cited

U.S. PATENT DOCUMENTS

| 5,796,859 A * | 8/1998 | Mammone ..................... 382/128 |
| 2007/0030946 A1 | 2/2007 | Tsuyuki et al. |
| 2009/0149734 A1 | 6/2009 | Sugiura |

FOREIGN PATENT DOCUMENTS

| JP | 2003-164445 | 6/2003 |
| JP | 2006-223333 | 8/2006 |
| JP | 2007-37782 | 2/2007 |
| JP | 2009-153965 | 7/2009 |

OTHER PUBLICATIONS

International Search Report in PCT/JP2010/069570.

* cited by examiner

*Primary Examiner* — Atiba O Fitzpatrick
(74) *Attorney, Agent, or Firm* — Cooper & Dunham LLP

(57) ABSTRACT

The X-ray CT apparatus which includes an X-ray generator and an X-ray detector for acquiring projection data of an object from plural angles and creates an arbitrary cross-sectional image of the object on the basis of the projection data includes: an extraction section which extracts a region, which includes a target organ moving periodically, from the cross-sectional image; a synchronous phase determination section which determines a synchronous phase, which is used when creating a synchronous cross-sectional image synchronized with periodic motion of the target organ, on the basis of continuity of the target organ in a direction perpendicular to the cross-sectional image; a synchronous cross-sectional image creating section which creates the synchronous cross-sectional image on the basis of projection data corresponding to the synchronous phase determined by the synchronous phase determination section; and a display unit which displays the synchronous cross-sectional image.

10 Claims, 8 Drawing Sheets

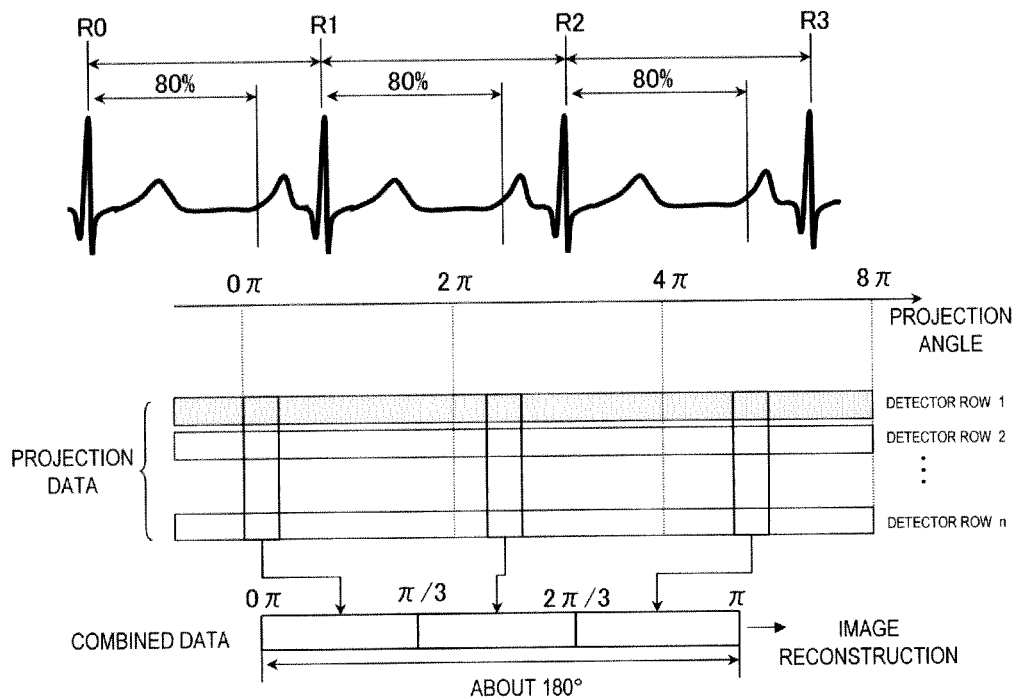
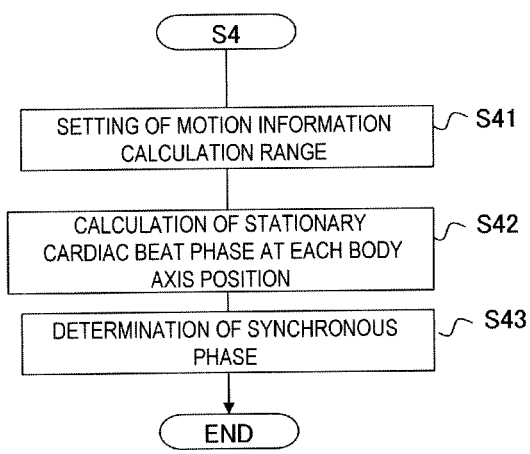

X-RAY CT APPARATUS AND IMAGE DISPLAY METHOD OF X-RAY CT APPARATUS

TECHNICAL FIELD

The present invention relates to an X-ray CT (Computed Tomography) apparatus and an image display method of an X-ray CT apparatus and in particular, to a technique for creating a three-dimensional image of a moving organ.

BACKGROUND ART

When a moving organ is photographed by an X-ray CT apparatus, artifacts due to motion, so-called motion artifacts are caused in an obtained cross-sectional image. As a typical method of reducing the motion artifacts, there is a method of controlling the acquisition timing of projection data or processing the acquired projection data on the basis of an electric signal acquired by measurement using biological sensors, such as an electrocardiograph or a respiratory sensor. Taking the photographing of a heart as an example, there is a method in which an electric signal acquired by measurement using an electrocardiograph, that is, electrocardiographic information is collected together with projection data and projection data corresponding to an arbitrary cardiac beat phase is extracted from the collected projection data on the basis of the acquired electrocardiographic information to perform image reconstruction and as a result, a cross-sectional image of the heart corresponding to the cardiac beat phase is obtained. This method is called an electrocardiographic synchronous reconstruction method.

In order to reduce motion artifacts in the electrocardiographic synchronous reconstruction method, it is important to designate as an optimal phase a cardiac beat phase corresponding to the projection data used for the image reconstruction, for example, to designate a cardiac beat phase with the smallest amount of movement of the heart. PTL 1 discloses an X-ray CT apparatus which calculates the amount of movement between cardiac beat phases by performing an addition process on the projection data and determines a low-motion cardiac beat phase on the basis of the amount of movement.

Citation List

Patent Literature

[PTL 1] JP-A-2007-37782

OUTLINE OF THE INVENTION

Problems to be Solved by the Invention

However, PTL 1 is a method for reducing motion artifacts in one cross-sectional image, and consideration for a three-dimensional image created by stacking or the like of plural cross-sectional images in the body axis direction has not been made. In general, if the position of an organ is different, the amount and direction of the movement due to cardiac beats are different. Accordingly, a cardiac beat phase with the small amount of movement also changes with the position of the organ. When image reconstruction is performed by determining a cardiac beat phase without taking into consideration that the cardiac beat phase with the small amount of movement changes with the position of the organ, the image quality degrades in other portions even if degradation of image quality in some portions of the three-dimensional image can be prevented, and the continuity of the three-dimensional image is adversely effected accordingly. This may cause a problem in diagnostic imaging. In particular, when diagnosing a hollow organ, such as a coronary artery, it is desirable to maintain the same image quality in the traveling direction of the organ. That is, it is preferable that the three-dimensional image be continuous.

Therefore, it is an object of the present invention to provide an X-ray CT apparatus, which creates and displays a three-dimensional image with high continuity for a moving organ, and an image display method of the X-ray CT apparatus.

Solution to Problem

In order to achieve the above-described object, the present invention is an X-ray CT apparatus which determines a specific phase, among phases indicating motion information of an organ in an object, as a synchronous phase on the basis of the continuity of a three-dimensional image in the body axis direction or the continuity of the organ in the traveling direction and performs image reconstruction using projection data corresponding to the determined synchronous phase and an image display method of the X-ray CT apparatus.

Specifically, the present invention is an X-ray CT apparatus which includes an X-ray generator and an X-ray detector for acquiring projection data of an object from plural angles and creates an arbitrary cross-sectional image of the object on the basis of the projection data. The X-ray CT apparatus includes: an extraction section which extracts a region, which includes a target organ moving periodically, from the cross-sectional image; a synchronous phase determination section which determines a synchronous phase, which is used when creating a synchronous cross-sectional image synchronized with periodic motion of the target organ, on the basis of continuity of the target organ in a direction perpendicular to the cross-sectional image; a synchronous cross-sectional image creating section which creates the synchronous cross-sectional image on the basis of projection data corresponding to the synchronous phase determined by the synchronous phase determination section; and a display unit which displays the synchronous cross-sectional image.

In addition, the present invention is an image display method of an X-ray CT apparatus which includes an X-ray generator and an X-ray detector for acquiring projection data of an object from plural angles and creates an arbitrary cross-sectional image of the object on the basis of the projection data. The image display method of an X-ray CT apparatus includes: an extraction step which extracts a region, which includes a target organ moving periodically, from the cross-sectional image; a synchronous phase determination step which determines a synchronous phase, which is used when creating a synchronous cross-sectional image synchronized with periodic motion of the target organ, on the basis of continuity of the target organ in a direction perpendicular to the cross-sectional image; a synchronous cross-sectional image creating step which creates the synchronous cross-sectional image on the basis of projection data corresponding to the synchronous phase determined in the synchronous phase determination step; and a display step which displays the synchronous cross-sectional image.

Advantage of the Invention

According to the present invention, it is possible to provide an X-ray CT apparatus, which creates and displays a three-dimensional image with high continuity for a moving organ, and an image display method of the X-ray CT apparatus.

BRIEF DESCRIPTION OF THE DRAWINGS

FIG. 3 is a view illustrating an electrocardiographic synchronous reconstruction method.

FIG. 4 is a view showing an example of the flow of processing for determining a synchronous phase.

MODE FOR CARRYING OUT OF THE INVENTION

Figure 1:
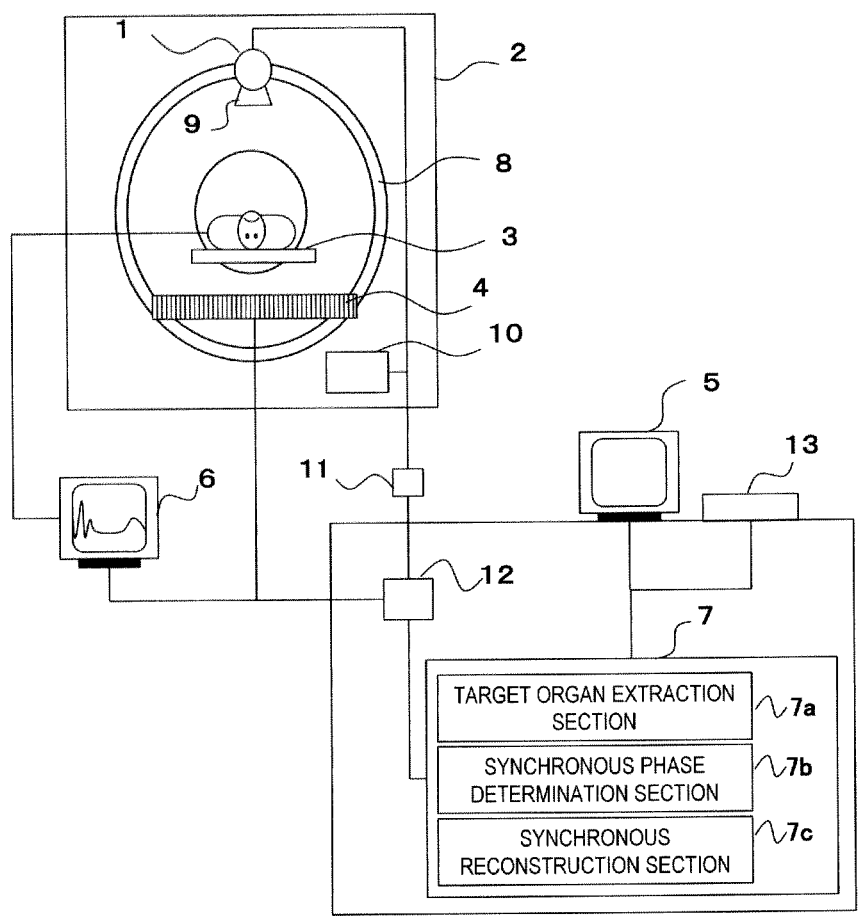
FIG. 1 is a block diagram showing the entire configuration of an X-ray CT apparatus of the present invention.

Hereinafter, preferred embodiments of an X-ray CT apparatus of the present invention will be described according to the accompanying drawings. In addition, in the following explanation and the accompanying drawings, the same reference numerals are given to components with the same functions, and repeated explanation thereof will be omitted.

FIG. 1 is a block diagram showing an entire configuration of an X-ray CT apparatus. The X-ray CT apparatus includes an X-ray generator 1, a scanner gantry unit 2, a patient table 3, an X-ray detector 4, a display unit 5, a periodic motion information acquisition unit 6, an image processing unit 7, a rotating disk 8, a collimator 9, a rotation driving unit 10, a measurement controller 11, a computer 12, and an input unit 13.

The X-ray generator 1 is a device which generates X-rays emitted to an object on the patient table 3. The collimator 9 is a device which limits an emission range of the X-rays generated by the X-ray generator 1. The X-ray detector 4 is a device which is disposed opposite the X-ray generator 1 in order to detect X-rays transmitted through the object. In the rotating disk 8, the X-ray generator 1 and the X-ray detector 4 are mounted. The rotating disk 8 rotates around the object with a driving force of the rotation driving unit 10. The scanner gantry unit 2 includes the X-ray generator 1, the patient table 3, the X-ray detector 4, the rotating disk 8, the collimator 9, and the rotation driving unit 10 therein.

The input unit 13 is a device for inputting an object name, examination date and time, photographing conditions, image processing conditions, and the like. Specifically, the input unit 13 is a keyboard or a pointing device. The image processing unit 7 is a device which creates projection data from measurement data of the transmitted X-rays detected by the X-ray detector 4 and performs image reconstruction processing on the projection data to create a cross-sectional image of the object. In addition, the image processing unit 7 will be described in detail later. The display unit 5 is a device which displays the cross-sectional image created by the image processing unit 7, the photographing conditions set through the input unit 13, and the like. Specifically, the display unit 5 is a CRT (Cathode-Ray Tube), a liquid crystal display, or the like. The computer 12 is a device which controls the image processing unit 7, the measurement controller 11, or the like on the basis of the photographing conditions, the image processing conditions, and the like input through the input unit 13.

The measurement controller 11 is a device which controls the intensity of the X-rays generated by the X-ray generator 1, the driving force of the rotation driving unit 10, and the like according to an instruction from the computer 12. The periodic motion information acquisition unit 6 is a device which acquires periodic motion information of an organ in the object, for example, cardiac motion, motion due to breathing, and the like. For example, the periodic motion information acquisition unit 6 is an electrocardiograph or a respiratory sensor. In addition, the periodic motion information acquisition unit 6 may be a device which receives the periodic motion information acquired from an analysis result of the projection data created by the image processing unit 7. For example, the analysis result of the projection data is periodic motion information obtained by calculating the difference of projection data in the opposite relationship, periodic motion information which is calculated from changes in a position of the center of gravity after calculating the position of the center of gravity of the projection data in the channel direction of the X-ray detector 4 at each projection angle, or the like. Although the periodic motion information acquisition unit 6 is set as an electrocardiograph in the following explanation, the periodic motion information acquisition unit 6 is not limited to this.

The image processing unit 7 has a target organ extraction section 7a, a synchronous phase determination section 7b, and a synchronous reconstruction section 7c as functions other than the above-described function of creating the projection data or the cross-sectional image. The target organ extraction section 7a extracts an organ to be diagnosed from a three-dimensional image, which is created by stacking of cross-sectional images or the like, in a three-dimensional manner by threshold value processing or the like. The synchronous phase determination section 7b calculates motion information of the target organ extracted by the target organ extraction section 7a and determines a synchronous phase, which is used when creating a synchronous cross-sectional image, from the calculated motion information. The synchronous reconstruction section 7c creates the synchronous cross-sectional image on the basis of the projection data corresponding to the synchronous phase determined by the synchronous phase determination section 7b.

First Embodiment

Figure 2:
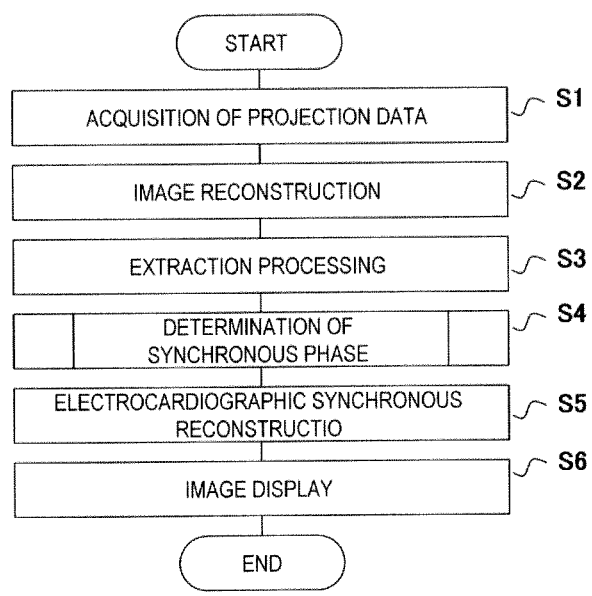
FIG. 2 is a view showing the flow of processing in a first embodiment of the present invention.

FIG. 2 is a view showing the flow of processing in a first embodiment of the present invention. Hereinafter, each step in FIG. 2 will be described in detail. In addition, although heart photographing will be described below, objects to be photographed are not limited to the heart. For example, the object to be photographed may be an organ around the heart which moves according to a cardiac beat and may be an organ moving according to breathing.

(Step S1)

The computer 12 executes heart photographing by controlling the periodic motion information acquisition unit 6, the image processing unit 7, the measurement controller 11, and the like on the basis of the photographing conditions set through the input unit 13. As a result, the projection data is acquired together with electrocardiographic information. Moreover, in order to acquire the projection data, projection data of heart photographing performed in the past may be read from a storage device or a database on a network together with the electrocardiographic information.

(Step S2)

The image processing unit 7 creates a cross-sectional image of the heart by performing image reconstruction of the projection data acquired in step S1. Since the cross-sectional image reconstructed in this step is not a final result, a general image reconstruction method may be used. However, in order to improve the processing accuracy after this step, in particular, in order to execute extraction processing performed in step S3 with high precision, it is preferable to create a cross-sectional image after reducing motion artifacts using electrocardiographic synchronous reconstruction. In the present embodiment, a case will be described in which the electrocardiographic synchronous reconstruction is used.

Although there are some methods for the electrocardiographic synchronous reconstruction, a method called division type electrocardiographic synchronous reconstruction is used to improve the time resolution. The division type electrocardiographic synchronous reconstruction is a method of creating one cross-sectional image by combining the projection data of plural cardiac beats. FIG. 3 shows an example thereof. FIG. 3 shows an example of creating a cross-sectional image when a relative value of a cardiac beat phase, which is standardized as 0 to 100% between adjacent R waves, is 80%. In FIG. 3, divided projection data with different projection angles in the same cardiac beat phase is extracted from the projection data acquired in three cardiac beats, and projection data of about 180° which is a projection angle required for reconstruction of one cross-sectional image is combined. In this example, divided projection data of $0\pi$ to $\frac{1}{3}\pi$ is extracted from the projection data between R0 and R1, divided projection data of $\frac{1}{3}\pi$ to $\frac{2}{3}\pi$ is extracted from the projection data between R1 and R2, and divided projection data of $\frac{2}{3}\pi$ to $\pi$ is extracted from the projection data between R2 and R3. Image reconstruction is performed on projection data of about 180° obtained by combining these divided projection data items. In addition, in order to create a cross-sectional image at a body axis position where no projection data is acquired, interpolation processing between the projection data acquired by each row of detectors arrayed in the body axis direction is performed to create interpolated projection data as projection data equivalent to the body axis position, and image reconstruction is performed.

(Step S3)

The target organ extraction section 7a performs processing of extracting an organ, which is to be diagnosed, from a three-dimensional image obtained by stacking or the like of the cross-sectional image created in step S2. Threshold value processing, such as a region growing method, may be used for extraction of an organ. In order to use the region growing method or the like, it is necessary to set an extraction start point. The extraction start point may be set automatically from anatomical features of the organ, or an operator may designate the extraction start point on the cross-sectional image created in step S2 using the input unit 13.

(Step S4)

The synchronous phase determination section 7b determines a synchronous phase, which is used when electrocardiographic synchronous reconstruction of the organ extracted in step S3 is performed in step S5, on the basis of the continuity of the extracted organ in the body axis direction. In order to determine the synchronous phase used in step S5, it is necessary to acquire the motion information in advance. In the case of the heart, a method of acquiring the electrocardiographic information by measurement using an electrocardiograph is generally used. Examples of other methods include a method of taking the image data difference between cardiac beat phases, a method of taking the projection data difference between cardiac beat phases, and a method of taking the difference between opposite projection data. In the present embodiment, any method may be used.

By analyzing the acquired motion information, the synchronous phase used in step S5 can be determined on the basis of the continuity of the extracted organ in the body axis direction. In a typical cardiac examination, diagnosis is performed using image data in a cardiac beat phase with the smallest amount of movement. Hereinafter, the cardiac beat phase with the smallest amount of movement will be called a stationary cardiac beat phase, and a method of determining the synchronous phase used in step S5 on the basis of the stationary cardiac beat phase at each position in the body axis direction will be described. In addition, the synchronous phase is not limited to the stationary cardiac beat phase, and may be any phase.

FIG. 4 is a view showing an example of the flow of processing in step S4. Hereinafter, each step in FIG. 4 will be described in detail.

(Step S41)

The synchronous phase determination section 7b sets a motion information calculation range. The motion information calculation range may be the entire range of the cross-sectional image or may be a limited range on the cross-sectional image. By limiting the calculation range, it is possible to suppress an influence of the movement of other organs, for example, an influence of a movement of a bone or a contrast agent of a cardiac lumen. In addition, the amount of calculation after this step can be reduced by limiting the calculation range.

In order to set the calculation range, the calculation range may be calculated by multiplying the size of the organ extracted in step S3 by a predetermined rate, the calculation range of each organ registered in advance may be read, or the operator may set the calculation range on a cross-sectional image by operating the input unit 13. In addition, it is also possible to calculate the position of the organ extracted in each cardiac beat phase and to set the range of the calculated position as the motion information calculation range.

Figure 5:
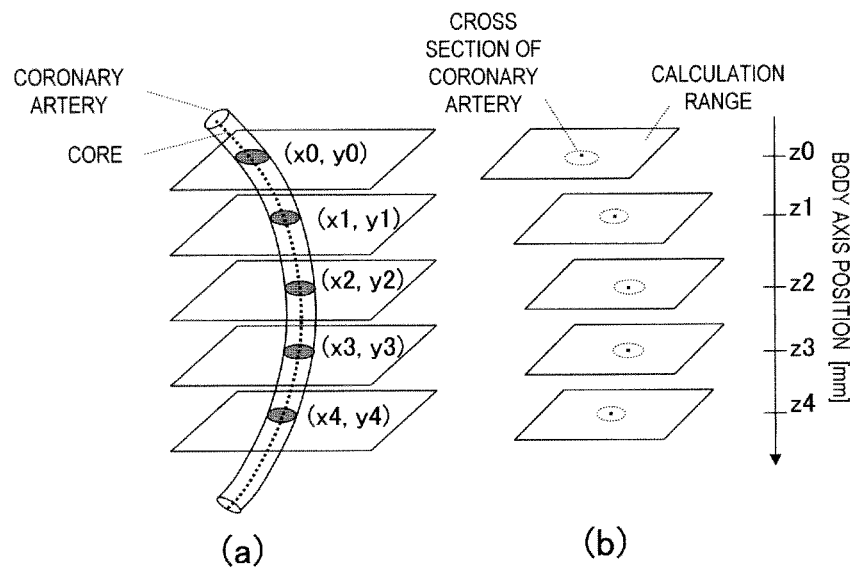
FIG. 5 is a view illustrating a method of setting a motion information calculation range on a cross section perpendicular to the body axis direction.

FIG. 5 shows an example of a method of setting the motion information calculation range. FIG. 5(a) shows a case where the target organ extracted in step S3 is a coronary artery. First, the coordinates of a core of the coronary artery extracted at positions z0 to z4 in the body axis direction, at which the motion information is calculated, are calculated. In FIG. 5(a), the coordinates of the core in the body axis position z0 are (x0, y0), the coordinates of the core in the body axis position z1 are (x1, y1), the coordinates of the core in the body axis position z2 are (x2, y2), the coordinates of the core in the body axis position z3 are (x3, y3), and the coordinates of the core in the body axis position z4 are (x4, y4). Next, at each body axis position, the motion information calculation range is set with the calculated coordinates of the core as its center. FIG. 5 (b) shows an example of the set motion information calculation range. The shape of the calculation range may be a rectangle as shown in FIG. 5(b), or may be a circle.

Figure 6:
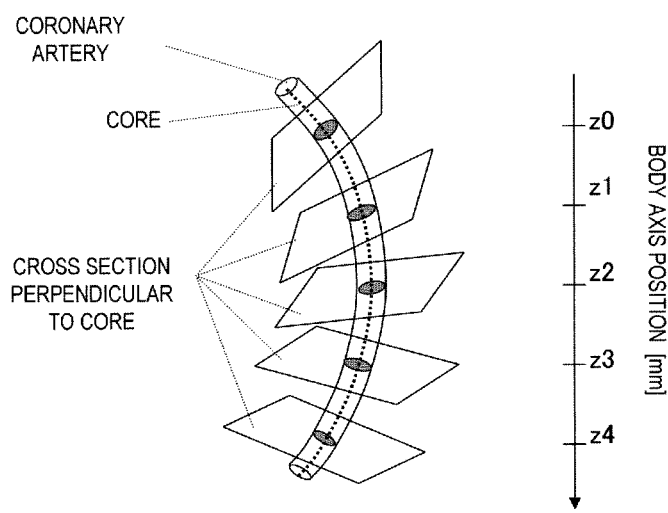
FIG. 6 is a view illustrating a method of setting the motion information calculation range on a cross section perpendicular to the traveling direction of an organ.

In addition, the motion information calculation range may be a range on the cross section perpendicular to the body axis direction as shown in FIG. 5, or may be a range on the cross section perpendicular to the traveling direction of the organ as shown in FIG. 6, that is, a range on the cross section perpendicular to the core of the coronary artery. When placing emphasis on the continuity of a hollow organ, such as the coronary artery, in its traveling direction, it is preferable to calculate the motion information at different positions in the traveling direction with the same index. In this case, therefore, it is preferable to set the motion information calculation range on the cross section perpendicular to the traveling direction of the organ. In order to acquire the cross section perpendicular to the traveling direction of the organ, it is preferable to create a desired cross-sectional image, that is, a cross-sectional image perpendicular to the traveling direction of the organ on the basis of the three-dimensional image obtained by stacking or the like of the cross-sectional image created in step S2.

In addition, when the target organ is not the coronary artery but the entire heart, the motion information calculation range may be set on a cross-sectional image perpendicular to a long axis, which is a longitudinal direction of the heart, or may be set on a cross-sectional image including the long axis, that is, on a cross-sectional image perpendicular to the cross-sectional image perpendicular to a long axis. Also in this case, it is preferable to create a cross-sectional image perpendicular to the long axis of the heart or a cross-sectional image including the long axis on the basis of the three-dimensional image.

(Step S42)

The synchronous phase determination section $7b$ calculates the stationary cardiac beat phase at each body axis position. An example of the procedure will be described. First, motion information of the target organ is calculated at each body axis position within the calculation range set in step S41. Then, the stationary cardiac beat phase at each body axis position is searched for by analyzing the calculated motion information. In order to search for the stationary cardiac beat phase at each body axis position, a known technique may be used. For example, it is preferable to search for a cardiac beat phase in which a brightness value of a difference image calculated between adjacent cardiac beat phases is smallest or to search for a cardiac beat phase in which the difference value between the opposite projection data is smallest.

Figure 7:
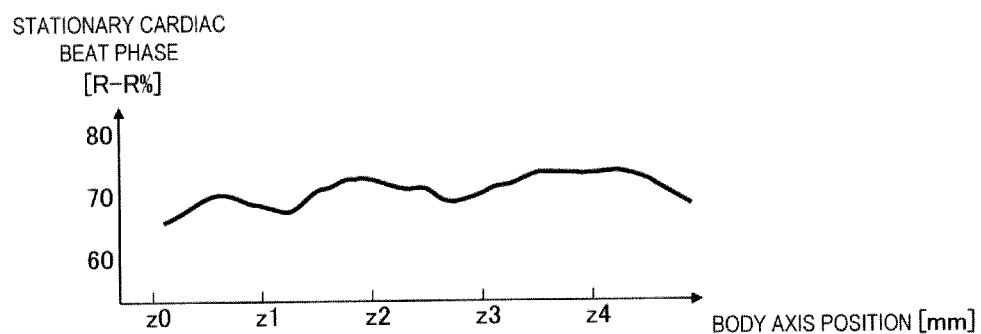
FIG. 7 is a view showing an example of the relationship between a stationary cardiac beat phase and a body axis position.

FIG. 7 shows an example of the relationship between the stationary cardiac beat phase and the body axis position, which is obtained from the stationary cardiac beat phase calculated at each body axis position. In FIG. 7, the vertical axis indicates the stationary cardiac beat phase, and the horizontal axis indicates the body axis position. The stationary cardiac beat phase is indicated by the relative value between adjacent R waves. As illustrated in FIG. 7, the stationary cardiac beat phase generally changes with the body axis position. This is because the amount and direction of the movement of an organ differ with each portion of the organ.

(Step S43)

From the relationship between the stationary cardiac beat phase and the body axis position illustrated in FIG. 7, the synchronous phase determination section $7b$ determines a phase used for the synchronous reconstruction performed in step S5 on the basis of the continuity in the body axis direction. Hereinafter, an example of a synchronous phase determination method based on the continuity in the body axis direction will be described.

For example, the relationship shown in FIG. 7 is used as it is, and the stationary cardiac beat phase at each body axis position is set as a synchronous phase. According to this determination method, an image with less motion artifacts can be obtained at all body axis positions. As a result, it is possible to obtain a three-dimensional image with high continuity of image quality in the body axis direction.

Figure 8:
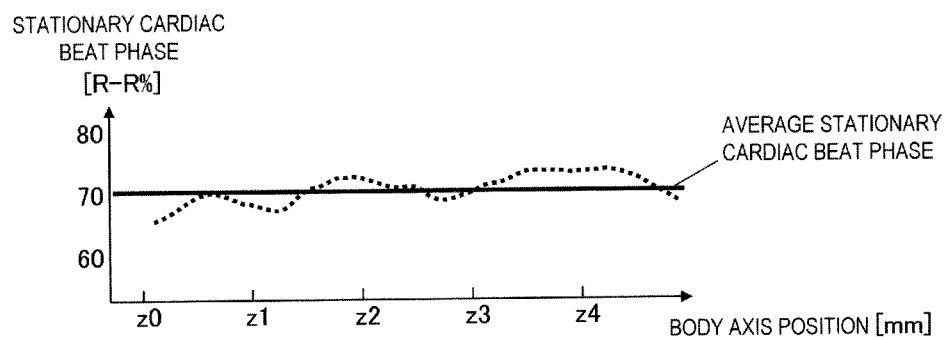
FIG. 8 is a view showing an example of an average stationary cardiac beat phase.

In FIG. 8, an average value of the stationary cardiac beat phase at each body axis position is calculated as an average stationary cardiac beat phase, and this average stationary cardiac beat phase is set as a synchronous phase at all axis positions. According to this determination method, synchronous reconstruction is performed using the same cardiac beat phase at all axis positions. As a result, the operation time required for the synchronous reconstruction in step S5 is shortened, and the image quality is not reduced at any body axis position. In addition, an image with high continuity of a cardiac beat phase in the body axis direction is acquired.

Figure 9:
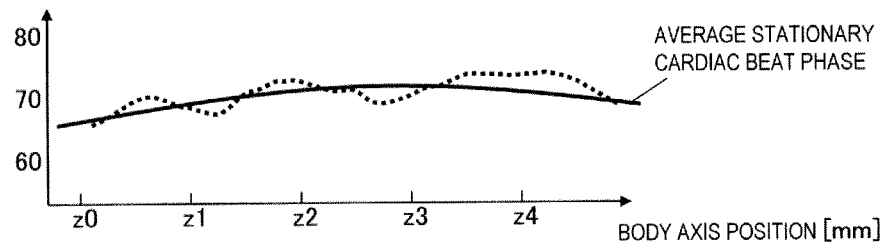
FIG. 9 is a view showing another example of the average stationary cardiac beat phase.

In FIG. 9, a moving average value of the stationary cardiac beat phase at each body axis position is calculated as the average stationary cardiac beat phase, and this average stationary cardiac beat phase is set as a synchronous phase. According to this determination method, a synchronous phase close to the stationary cardiac beat phase at each body axis position can be set while maintaining the continuity of the cardiac beat phase in the body axis direction. As a result, the image quality is not reduced at any body axis position.

In addition, it is also possible to display the graph shown in FIG. 8 or 9 on the display unit 5 so that fine adjustment of the calculated average stationary cardiac beat phase can be performed by operating a mouse or the like of the input unit 7.

Figure 10:
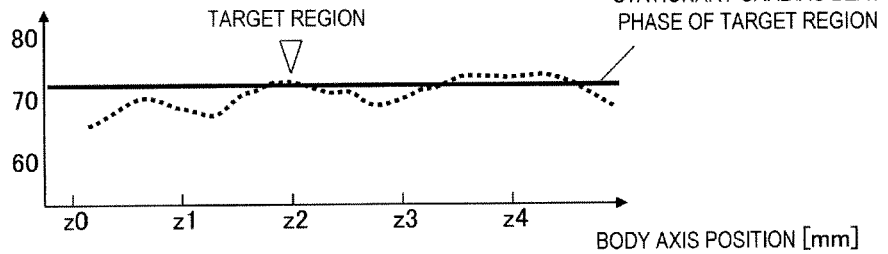
FIG. 10 is a view showing an example of a target region stationary cardiac beat phase.

In addition, although the stationary cardiac beat phase is set in the entire region in FIGS. 8 and 9, a cross-sectional image of the entire region may be created with a stationary cardiac beat phase in a target region to be carefully diagnosed. FIG. 10 shows an example when the stationary cardiac beat phase of the target region is set. When the stationary cardiac beat phase is set as shown in FIG. 10, it is possible to reduce motion artifacts of a cross-sectional image at the body axis position $z2$ equivalent to the target region. In addition, when there are the plural target regions, the average value of stationary cardiac beat phases of the target regions may be set as a synchronous phase. By performing this processing, it is possible to obtain an image in which the continuity of the cardiac beat phase in the body axis direction is high and there are less motion artifacts in the target region.

Figure 11:
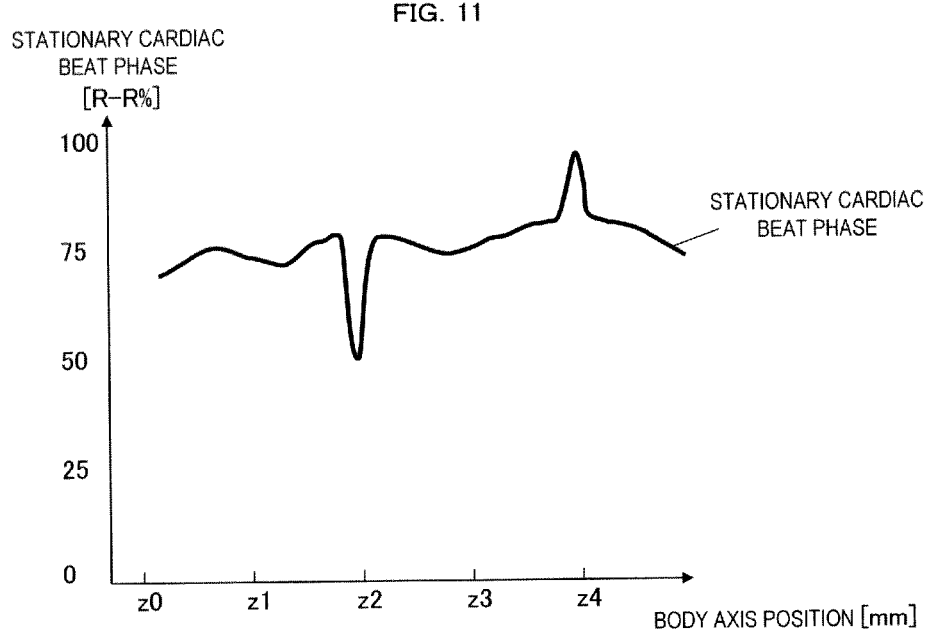
FIG. 11 is a view showing another example of the relationship between the stationary cardiac beat phase and the body axis position.

In addition, it is also possible to limit a search range of the stationary cardiac beat phase. When a sudden cardiac beat occurs during photographing or when there is an influence of the movement of a non-diagnostic portion, the stationary cardiac beat phases may be largely different in part. An example thereof is shown in FIG. 11. In FIG. 11, the stationary cardiac beat phases at the body axis positions $z2$ and $z4$ are largely different from those at the other body axis positions $z0$, $z1$, and $z3$. In such a case, if the average value of the stationary cardiac beat phases at the body axis positions $z0$ to $z4$ is calculated, the average value is largely different from each of the stationary cardiac beat phases at all body axis positions. This has an adverse effect on the continuity in the body axis direction. In such a case, the search range of the stationary cardiac beat phase may be limited using the continuity of the extracted organ in the body axis direction.

Figure 12:
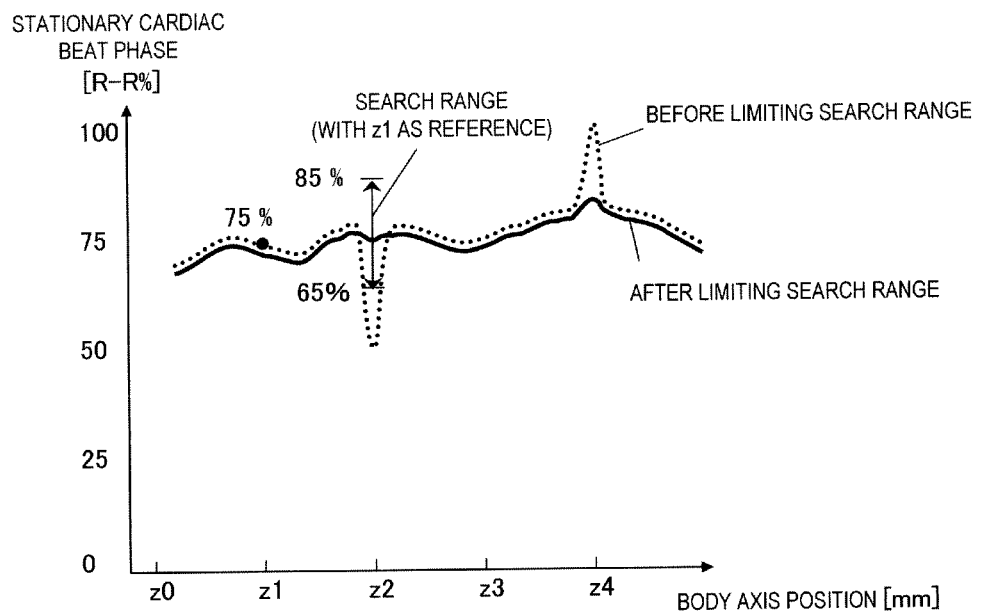
FIG. 12 is a view showing an example of the relationship between a body axis position and a stationary cardiac beat phase calculated by limiting a search range.

FIG. 12 shows an example when the search range of the stationary cardiac beat phase is limited. For example, when the stationary cardiac beat phase at z1 is calculated as 75%, a search range around 75% is set at the position z2 adjacent to z1, and a phase with the smallest amount of movement is set as the stationary cardiac beat phase. In the example shown in FIG. 12, the stationary cardiac beat phase at Z2 is calculated with ±10% from 75% as a search range. By repeatedly performing such search technique in the body axis direction, it is possible to extract projection data with less influence of the movement due to a cardiac beat on the whole while maintaining the continuity. In addition, the operation time can be shortened by limiting the search range of the stationary cardiac beat phase to a predetermined range instead of taking the entire range.

Using any of the methods described above or a method based on a combination of these methods, a synchronous phase used for the synchronous reconstruction performed in step S5 on the basis of the continuity in the body axis direction is determined.

(Step S5)

The synchronous reconstruction section 7c performs electrocardiographic synchronous reconstruction using the projection data corresponding to the synchronous phase determined on the basis of the continuity in the body axis direction in step S4. Thus, it becomes possible to obtain a cross-sectional image optimal for diagnosis of the target organ, for example, the coronary artery, by performing the electrocardiographic synchronous reconstruction in the synchronous phase determined on the basis of the continuity in the body axis direction.

(Step S6)

The computer 12 displays a three-dimensional image, which is created by stacking or the like of the cross-sectional image obtained in step S5, on the display unit 5. The operator diagnoses the target organ, for example, the coronary artery, by observing the three-dimensional image displayed on the display unit 5.

By performing the flow of such processing, it is possible to create and display a three-dimensional image with high continuity for the moving organ.

Second Embodiment

In the first embodiment, the method of extracting the target organ automatically has been described in step S3. In the present embodiment, a method of calculating the stationary cardiac time phase of a range set by the operator and updating a synchronous reconstruction image when necessary will be described.

Figure 13:
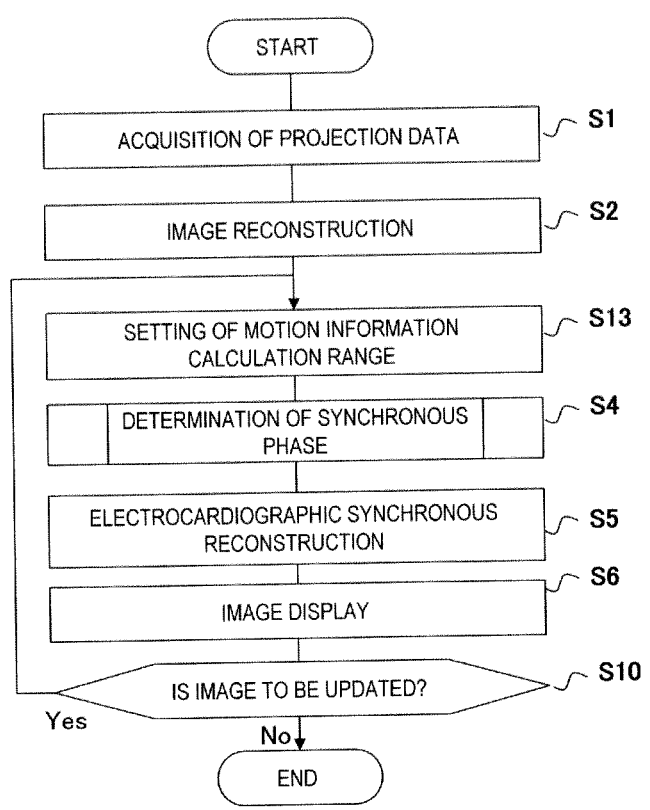
FIG. 13 is a view showing the flow of processing in a second embodiment of the present invention.

FIG. 13 is a view showing the flow of processing in a second embodiment of the present invention. Hereinafter, each step in FIG. 13 will be described in detail. In addition, the same step reference numerals are given to the same steps as in the first embodiment, and explanation thereof will be omitted.

(Steps S1 and S2)

Steps S1 and S2 are the same as those in the first embodiment.

(Step S13)

The computer 12 displays on the display unit 5 the cross-sectional image created in step S2 or an MPR (Multi Planar Reconstruction) image, which is an arbitrary cross-sectional image created on the basis of a three-dimensional image obtained by stacking or the like of the cross-sectional image. The operator sets a motion information calculation range on the cross-sectional image or on the MPR image using the input unit 13, such as a mouse. For example, a range including the coronary artery which is the target organ is set as the calculation range shown in FIG. 5. Alternatively, the cross-sectional image of the cross section perpendicular to the core shown in FIG. 6 may be displayed as the MPR image so that the calculation range is set on the MPR image.

(Steps S4 to S6)

Steps S4 to S6 are the same as those in the first embodiment. Then, in step S4, motion information in the calculation range set in step S13 is analyzed, and the stationary cardiac beat phase is determined as a synchronous phase.

(Step S10)

The operator determines whether or not to update the image displayed in step S6, and presses an image update button or an end button displayed on the display unit 5 using the input unit 13, such as a mouse. The computer 12 returns the process to step S13 when the pressing of the image update button is detected, and ends the process when the pressing of the end button is detected.

By performing the flow of such processing, a synchronous reconstruction image is updated, when necessary, at the position where the operator sets the calculation range for the moving organ.

In the example described above, the synchronous reconstruction is performed at each position where the calculation range is set. On the other hand, a stationary cardiac beat phase at each position where the calculation range is set may be stored in a storage area, and synchronous reconstruction processing may be performed collectively after stationary cardiac beat phases at all positions are determined.

DESCRIPTION OF REFERENCE NUMERALS AND SIGNS

1: X-ray generator
2: scanner gantry unit
3: patient table
4: X-ray detector
5: display unit
6: periodic motion acquisition unit
7: image processing unit
7a: target organ extraction section
7b: synchronous phase determination section
7c: synchronous reconstruction section
8: rotating disk
9: collimator
10: rotation driving unit
11: measurement controller
12: computer
13: input unit

The invention claimed is:

1. An X-ray CT apparatus which includes an X-ray generator and an X-ray detector for acquiring projection data of an object from a plurality of angles and creates an arbitrary cross-sectional image of the object on the basis of the projection data, the X-ray CT apparatus comprising:
an extraction section which extracts a region, which includes a target organ moving periodically, from the cross-sectional image;
a synchronous phase determination section which determines a synchronous phase, which is used when creating a synchronous cross-sectional image synchronized with periodic motion of the target organ, on the basis of continuity of the target organ in a direction perpendicular to the cross-sectional image;
a synchronous cross-sectional image creating section which creates the synchronous cross-sectional image on the basis of projection data corresponding to the synchronous phase determined by the synchronous phase determination section; and a display unit which displays the synchronous cross-sectional image.

2. The X-ray CT apparatus according to claim 1,
wherein the synchronous phase determination section determines the synchronous phase on the basis of a stationary phase which is a phase with a smallest amount of movement of the target organ.

3. The X-ray CT apparatus according to claim 2,
wherein the synchronous phase determination section calculates the stationary phases at respective different positions in the direction perpendicular to the cross-sectional image and determines as the synchronous phase an average value of the stationary phases calculated at the respective positions.

4. The X-ray CT apparatus according to claim 2,
wherein the synchronous phase determination section determines the stationary phase at a position, which is designated from different positions in the direction perpendicular to the cross-sectional image, as the synchronous phase.

5. The X-ray CT apparatus according to claim 2,
wherein the synchronous phase determination section searches for a second stationary phase in a limited phase range and determines the second stationary phase as the synchronous phase.

6. The X-ray CT apparatus according to claim 1,
wherein the synchronous phase determination section determines the synchronous phase on the basis of continuity of the target organ in a longitudinal direction.

7. The X-ray CT apparatus according to claim 6,
wherein the target organ is a hollow organ, and the synchronous phase determination section determines the synchronous phase on the basis of continuity of the hollow organ in a traveling direction.

8. The X-ray CT apparatus according to claim 1,
wherein the target organ is an organ moving according to a cardiac beat, and
a phase of periodic motion of the target organ is a cardiac beat phase.

9. The X-ray CT apparatus according to claim 1,
wherein the target organ is an organ moving according to breathing, and
a phase of periodic motion of the target organ is a breathing phase.

10. An image display method of an X-ray CT apparatus which includes an X-ray generator and an X-ray detector for acquiring projection data of an object from a plurality of angles and creates an arbitrary cross-sectional image of the object on the basis of the projection data, the image display method of an X-ray CT apparatus comprising:

an extraction step which extracts a region, which includes a target organ moving periodically, from the cross-sectional image;

a synchronous phase determination step which determines a synchronous phase, which is used when creating a synchronous cross-sectional image synchronized with periodic motion of the target organ, on the basis of continuity of the target organ in a direction perpendicular to the cross-sectional image;

a synchronous cross-sectional image creating step which creates the synchronous cross-sectional image on the basis of projection data corresponding to the synchronous phase determined in the synchronous phase determination step; and a display step which displays the synchronous cross-sectional image.

\* \* \* \* \*